United States Patent [19]

Cook

[11] Patent Number: 5,478,876
[45] Date of Patent: Dec. 26, 1995

[54] POLYMER DISPERSIONS STABILIZED BY FATTY ALCOHOL ALKOYLATES

[75] Inventor: Iain Cook, West Brunswick, Australia

[73] Assignee: ICI Australia Operations Proprietary Limited, Melbourne, Australia

[21] Appl. No.: 286,422

[22] Filed: Aug. 5, 1994

Related U.S. Application Data

[62] Division of Ser. No. 923,958, filed as PCT/AU90/00565, Nov. 23, 1990, published as WO91/13849, Sep. 19, 1991, Pat. No. 5,362,832.

[30] Foreign Application Priority Data

Nov. 23, 1990 [AU] Australia .................................. PJ9055

[51] Int. Cl.$^6$ ..................................................... C08L 33/00
[52] U.S. Cl. ........................ 524/376; 524/369; 524/556; 524/560; 524/832
[58] Field of Search ..................... 524/376, 369, 524/832

[56] References Cited

U.S. PATENT DOCUMENTS

| | | | |
|---|---|---|---|
| 4,396,779 | 8/1983 | Edwards | 568/618 |
| 5,362,832 | 11/1994 | Cook | 526/333 |

FOREIGN PATENT DOCUMENTS

| | | | |
|---|---|---|---|
| WO8912618 | 12/1989 | European Pat. Off. | C07C 43/16 |
| 0389179 | 9/1990 | European Pat. Off. | C08F 283/06 |
| 57-38892 | 3/1982 | Japan | C10L 5/00 |
| 61-47408 | 3/1986 | Japan | A61K 7/00 |

OTHER PUBLICATIONS

Jamieson, G. R. et al, J. Chromatog., 29:44–48 (1967).

*Primary Examiner*—Mark Nagumo
*Attorney, Agent, or Firm*—Cushman Darby & Cushman

[57] ABSTRACT

A compound of the formula

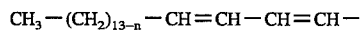

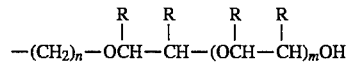

where R, which may be the same or different, is selected from at least one of hydrogen, methyl, ethyl and phenyl, at least one R on each —OCHR—CHR— unit being hydrogen; where m is an integer selected from 1–100; where n is an integer selected from 8 and 9. The preferred process of preparation is by the reaction of alkylene oxide with linoleyl alcohol in the presence of a catalyst which is a Bronsted base. The compounds are useful as reactive surfactants in aqueous emulsion polymerisation processes.

5 Claims, No Drawings

POLYMER DISPERSIONS STABILIZED BY FATTY ALCOHOL ALKOYLATES

This is a division of Application No. 07/923,958, filed as PCT/AU90/00565, Nov. 23, 1990, published as WO91/13849, Sep. 19, 1991, now U.S. Pat. No. 5,362,8321.

This invention relates to alkoxylates of unsaturated fatty alcohols and to their use in surface coating compositions.

It has been known for some time that it is possible to prepare molecules which consist of a hydrocarbon chain and an oxyalkylene chain (usually an oxyethylene chain), and such compounds have been useful, for example, as surfactants in a variety of end uses, one typical example being surface coatings. The hydrocarbon chain may be derived from a long chain fatty alcohol, a very common example being oleyl alcohol. This alcohol has a single double bond but this double bond is very unreactive under normal polymerisation conditions and oleyl ethoxylates have enjoyed wide use in many fields where the presence of this unsaturation is of no consequence.

In those cases where, in that part of the hydrocarbon alkoxylate which is lipophilic, there is desired the presence of unsaturation which is relatively reactive with respect to an addition polymerisation reaction, special compounds have been devised. Thus, while compounds such as oleyl ethoxylate will work in the multi-polymer particle dispersions disclosed in U.S. Pat. No. 4,413,073, the preferred unsaturated surfactants described in this disclosure are more reactive and the most preferred surfactants have multiple double bonds derived from such molecules as pentaerythritol triallyl ether. Similarly, in European Published Application 0 002 252, the applicants use allylic bonds for reaction with the fatty acid chains of the water-borne alkyd resin which is described in that document.

It has now been found that it is possible to provide an unsaturated fatty alcohol alkoxylate whose unsaturation is usefully reactive. There is therefore provided, according to the present invention, a compound of the formula I

$$CH_3-(CH_2)_{13-n}-CH=CH-CH=CH-$$

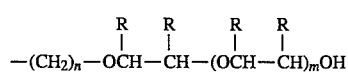
$$-(CH_2)_n-OCH-CH-(OCH-CH)_mOH$$
with R substituents where R, which may be the same or different, is selected from at least one of hydrogen, methyl, ethyl and phenyl, at least one R on each —OCHR—CHR— unit being hydrogen; where m is an integer selected from 1–100; where n is an integer selected from 8 and 9.

The oxyalkylene chain of the compound is of 2–101 and preferably 6–50 units in length. The nature of the individual units is very much determined by the end use to which the compound will be put. For example, if the compound is to be a reactive surfactant in an aqueous emulsion system, the oxyalkylene chain will consist mainly, and preferably solely, of oxyethylene units. Provided that the desired balance between the lipophilic and hydrophilic portions of the surfactant can be achieved, it is possible to include a proportion of oxypropylene, oxyethylethylene or oxyphenylethylene units. These are advantageously located on the chain adjacent to the lipophilic portion as they increase the overall lipophilicity of the molecule. The preferred oxyalkylene unit is the oxyethylene unit; those compounds according to the invention which comprise oxyalkylene units other than oxyethylene units are useful as intermediates for other products, but the oxyethylene unit is the most useful and preferably all of the oxyalkylene units are oxyethylene units.

It is particularly preferred that the double bonds in the compounds of the invention exhibit opposite geometrical isomerism, that is, one trans and the other cis, not both cis or trans.

Accordingly we provide in a particularly preferred embodiment of the invention a compound of formula I as hereinbefore described in which the double bonds exhibit opposite geometrical isomerism.

The compounds of this invention may be synthesised by any convenient means. A particularly valuable method of preparing the preferred compounds forms part of this invention. There is therefore provided a method of preparing a compound according to the invention comprising the reaction of alkylene oxide with linoleyl alcohol in the presence of a base catalyst which is a Bronsted base.

It will readily be appreciated that the structure of this alcohol is different to that of the non-oxyalkylene chain part of the compounds; linoleyl alcohol is cis-9, cis-12-octadecadienol. It has been found that, under the conditions of the alkoxylation, one of the double bonds positioned at the 9- or the 12- position moves into a conjugated arrangement with respect to the other, and at the same time this bond changes its stereochemical configuration such that there is one cis-bond and one trans-bond.

The linoleyl alcohol for use in this aspect of the invention may be a pure substance. Alternatively, it is possible to use one of the commercially-available mixtures of fatty alcohols which contain a significant proportion of linoleyl alcohol. It has been found that the alkoxylation of such mixtures can give a product which is acceptable for many uses and which is considerably cheaper than the alkoxylated pure alcohol. However, it is essential that at least 15% and preferably at least 40% by weight of the mixture be linoleyl alcohol. Examples of suitable commercially-available mixtures can be found in the "Ocenol" range of product of Henkel KGaA, one suitable one being the "110–130" grade.

The invention also, therefore, provides a chemical composition which is essentially a blend of alkoxylated fatty alcohols, at least 15% (preferably at least 40%) by weight of which are compounds of formula I— as hereinabove described.

By "Bronsted base" is meant a base which is capable of abstracting a proton. While any Bronsted base will work to some extent in the invention, it will readily be appreciated by the skilled worker that, for some bases, the obtaining of acceptable yields will require unacceptably long reaction times and/or unacceptably severe reaction conditions, and the use of such bases is not therefore a practical proposition. As a general rule, reaction times should be no longer than 48 hours and reaction conditions no more severe than 160° C. temperature and 1000 kPa pressure. Any Bronsted base which gives an acceptable yield under conditions such as these is especially preferred for use in this invention. Examples of preferred bases are the alkali metal and alkaline earth metal alkoxides and hydroxides, particularly sodium methoxide and potassium hydroxide. Other suitable bases include metal hydrides, such as sodium hydride.

The compounds of this invention are useful in a number of applications, but compounds with appropriate HLB values are especially useful as reactive surfactants in the formulation of aqueous dispersions for use in water-borne coating compositions. They are, for example, useful in the preparation of polymer particles.

In a further embodiment of the invention we therefore provide a process for preparation of polymer particles, the process comprising polymerising in aqueous media unsaturated monomer in the presence of at least one compound of formula I as hereinbefore described.

The nature of the unsaturated monomer is not narrowly critical and particles may be prepared by this process using a wide range of monomers commonly used in suspension and emulsion polymerisation, for example one or more of the monomers selected from the group of the $C_1$–$C_{12}$ (preferably the $C_1$–$C_4$) alkyl acrylates and methacrylates, (meth)allyl acrylates and methacrylates, glycidyl methacrylate and vinyl acetate, hydroxy, butyl acrylate, 2-ethoxy ethyl acrylate, glycidyl acrylate, methyl methacrylate, ethyl methacrylate, butyl methacrylate, stearyl methacrylate, methacrylic acid, methoxy propyl methacrylate, cyclohexyl methacrylate, benzyl methacrylate, hydroxyethyl methacrylate, hydroxy propyl methacrylate, dimethylaminoethyl methacrylate, N-butoxymethyl methacrylamine, N-buoxymethyl acrylamide, glycidyl methacrylate, vinyl acetate, vinyl propionate, styrene, 1-methyl styrene, vinyl toluene, methoxy styrene and vinyl pyridine, di-butyl maleate and vinyl chloride.

The known techniques of suspension and emulsion polymerisation, including the selection of appropriate polymerisation initiators, are applicable to the preparation of the aqueous dispersion of our invention. As is understood in the art polar monomers may need to be used in combination with less polar monomers to achieve the appropriate aqueous dispersion. Either thermally-activated or redox initiators may be used.

Due to the reactivity of the compounds of formula I they have been found to provide a particularly stable dispersion of polymer particles therefore providing a significant improvement in aqueous coating compositions. In such applications, the compounds of formula I may be used alone or in combination with other surfactants, for example anionic surfactant. We therefore further provide an aqueous dispersion of polymer particles stabilized by at least one compound of formula I according to any one of claims 1 to 5.

The aqueous dispersion may comprise additives which adapt it for use as a coating composition.

Coating compositions may be prepared by blending standard additives such as pigments, extenders, antifoams, thickeners and fungicides into the dispersion in art-recognized quantities using known methods.

An example of polymer particles which may be produced using the compounds of formula I is described in U.S. Pat. No. 4,413,073.

A further particularly preferred example of polymer particles which may be prepared using compounds of formula I are core-sheath particles of the type described in Australian Patent Application No. 52006/90. Such particles will have diameters of less than 100 nm and comprise a core of polymer of an ethylenically unsaturated monomer and a sheath comprising polyoxyalkylene chains wherein said polyoxyalkylene chains are derived from the covalent bonding of compounds of formula I with the core addition-polymer.

The invention is further described with reference to the following example in which all parts are expressed by weight.

EXAMPLE 1

Preparation of compounds according to the invention, the compounds having 12 moles ethylene oxide per mole of unsaturated chain.

49.6 parts of linoleyl alcohol (cis-9-cis-12-octadien-1-ol; 99% ex Sigma) was, dissolved in 250 parts xylene containing 0.03 parts each of phenothiazine and 4-methoxyphenol. 1.8 parts 30% sodium methoxide in methanol was then rapidly added to the stirred solution which was then transferred to a clean dry stainless steel autoclave at 35° C. under slight vacuum. A further 50 parts xylene was used to rinse the residues from the flask and the line. The reactor was twice evacuated and purged with nitrogen, then heated under vacuum to 70° C., at which point xylene began to distil over. The autoclave was evacuated and purged with nitrogen once more, and was then pressurised to 70 kPa and heated to 140° C. Ethylene oxide (98 parts) was charged batchwise over 2 h, keeping the temperature below 143° C. and the pressure below 400 kPa. The reaction mixture was allowed to react out at 142±2° C. over 1½ h, cooled to 55° C., evacuated and purged and discharged into a solution of 0.84 parts of orthophosphoric acid in 5 parts water. Volatiles were removed under vacuum (rotary evaporator followed by oil pump at 0.5–1 mm Hg) at 70° C. The product, a pale yellow oil was filtered through "Celite" whilst warm. The cloud point (10% w/w in water) was 77°–77.5° C. Carbon-13 NMR showed that the linolenyl alcohol double bond peaks (127.95, 128.02, 130.12, 130.20 ppm from tetramethylsilane (TMS)) had disappeared, to be replaced by peaks due to the cis-9-trans-11 and trans-10-cis-12 isomers in approximately equal proportions (125.60, 128.59/128.62, 129.93/129.99, 134.59 ppm from TMS).

EXAMPLE 2

Preparation of compounds according to the invention from a commercially-available alcohol mixture, the compounds having 10 moles ethylene oxide per mole of unsaturated chain.

616 parts of "Ocenol" (Trade Mark) 110–130 (ex Henkel KGaA), (a commercially available mixture of fatty alcohols being approximately 40% by weight linoleyl alcohol) was warmed to dissolve any separated components. It was then charged to an autoclave and purged with nitrogen. There was then slowly added 18 parts of 30% sodium methoxide. The vessel containing the sodium methoxide was rinsed three times with 15 parts ethanol and this ethanol slowly charged with stirring. The autoclave was evacuated, purged with nitrogen and then evacuated and heated to 130° C., all volatile materials being stripped off. The evacuation and purging with nitrogen was repeated and 1034 parts ethylene oxide was then added over a period of 2 hours, the autoclave being maintained at 130°–145° C. and 100–500 kPa pressure. Reaction was continued for 30 minutes, and the contents of the autoclave were then cooled and volatiles were stripped off under vacuum. The cloud point of a 10% w/w mixture with water was found to be 71.5° C.–72.5° C. The pH of the product was reduced to 5.5 by the addition of an 85% solution of orthophosphoric acid in distilled water (9 parts was needed). The product was finally stripped under vacuum at 115° C. for 3 hours and filtered while hot through "Celite".

The final component was a pale orange-yellow solid. NMR analysis showed that the 9,12-arrangement of the double bonds of the linoleyl alcohol had changed to a mixture of 9,11- and 10,12-arrangements, to give compounds according to invention.

EXAMPLE 3

Preparation of compounds according to the invention, the compounds having the approximate composition 1 mole unsaturated chain to 40 moles ethylene oxide.

The compound was made in an analogous manner to example 2, with 185 parts "Ocenol" 110–130 and 1215 parts ethylene oxide. The product was an off-white solid which NMR analysis showed to consist mainly of a mixture of oleyl, 9,11- and 10,12-double bond-containing compounds.

EXAMPLE 4

Preparation of compounds according to the invention using two alkylene oxides (in this case propylene and ethylene oxides in the approximate unsaturated chain: propylene oxide:ethylene oxide mole ratio of 1:4:10).

"Ocenol" 110–130 (449 parts) was charged into a clean, dry autoclave at 50° C. and evacuated and purged with nitrogen. 18.0 parts 30% sodium methoxide in methanol, followed by 3×20 ml. rinse methanol was then charged to the autoclave with stirring. The reactor was evacuated and purged and then heated to 120° C. under vacuum. Propylene oxide (400 parts) was added over 2 h at 130°–135° C. and 100–200 kPa pressure. The reaction contents were reacted out for 1½ h and the reactor was then evacuated and purged to remove any residual propylene oxide. Ethylene oxide (753 parts) was then added over 1.2 h, reacted out for 1 h, cooled to 75° C., stripped under vacuum and neutralised with 10.4 parts 854 phosphoric acid in 60 ml water. The product, a pale orange-yellow liquid, was dehydrated under vacuum to 120° C. for 3 h and filtered while hot through "Celite". The cloud point of a 10% w/w solution was 55.5°–56.5° C. NMR analysis confirmed the alteration of the 9,12-unsaturated double bond arrangement into a mixture of 9,11- and 10,12-arrangements.

EXAMPLE 5

The use of a compound according to the present invention in the preparation of an aqueous dispersion of addition polymer particles.

The materials and quantities used were as follows:

| Stage | | | |
|---|---|---|---|
| A | deionised water | 106.74 | parts |
| | "Fenopon" (trade mark) CO 436 surfactant | 3.30 | |
| | 30% HCl | 3 | drops |
| | 1% ferrous sulphate solution | 4.18 | |
| B | t-butyl perbenzoate | 0.18 | |
| C | methyl methacrylate | 113.37 | |
| | butyl acrylate | 97.77 | |
| | methacrylic acid | 3.00 | |
| | compound from Example 2 | 15.62 | |
| D | deionised water | 143.81 | |
| | sodium erythorbate (10% aqueous solution) | 10.49 | |
| E | t-butyl perbenzoate | 1.54 | |

The stage A materials were added to a reaction vessel (the hydrochloric acid being sufficient to reduce the pH of the mixture to about 2) and were stirred under nitrogen for about 20 minutes.

The stage C monomers were mixed in another vessel and the Example 2 compound melted and added to them. The stage D materials were then added to the stage C materials and the resultant mixture was mixed vigorously to form a coarse emulsion.

The tert-butyl perbenzoate of stage B was added to the stage A materials in the reaction vessel and stirring was continued for 10 minutes to emulsify it. 10% of the stage C+stage D mixture was then added and stirred in, stirring was stopped and the mixture allowed to exotherm, cooling being applied to keep the temperature below 30° C.

After 30 minutes, the stage E tert-butyl perbenzoate was added to the reaction vessel with stirring and the remainder of the stage C+stage D materials fed in over a period of 80 minutes, maintaining the temperature at 30° C. When addition was complete, stirring and cooling were continued for a further 60 minutes. After cooling to 20° C., ammonium hydroxide solution was added to raise the pH to 8.5.

The resulting product was a fine particle size (83 nm average diameter measured using a "Nanosizer") aqueous dispersion of 46.0% solids contents.

The claims defining the invention are as follows:

1. An aqueous dispersion of polymer particles stabilised by at least one compound of the formula I

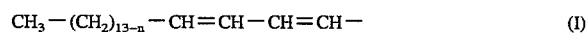

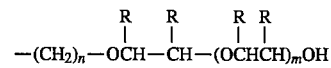

where R, which may be the same or different, is selected from the group consisting of hydrogen, methyl, ethyl and phenyl, at least one R on each —OCHR—CHR— unit being hydrogen; where m is an integer selected from the group consisting of 1–100; where n is an integer selected from the group consisting of 8 and 9.

2. An aqueous dispersion according to claim 1, the dispersion being in a form suitable for use as a coating composition.

3. An aqueous dispersion according to claim 1 wherein the compound of formula I is one wherein the double bonds exhibit opposite geometrical isomerism.

4. An aqueous dispersion according to claim 3 wherein the compound of formula I is one wherein m is an integer selected from the group consisting of 6–50.

5. An aqueous dispersion according to claim 4 wherein the compound of formula I is one wherein most or all of the groups R are hydrogen.

* * * * *